(12) United States Patent
Hagen

(10) Patent No.: US 8,143,041 B2
(45) Date of Patent: Mar. 27, 2012

(54) METHOD OF STIMULATING ETHANOL PRODUCTION AND GROWTH OF AQUATIC PLANTS

(75) Inventor: Tony A. Hagen, Sioux Falls, SD (US)

(73) Assignee: Aquatech Bioenergy LLC, Sioux Falls, SD (US)

( * ) Notice: Subject to any disclaimer, the term of this patent is extended or adjusted under 35 U.S.C. 154(b) by 356 days.

(21) Appl. No.: 12/437,333

(22) Filed: May 7, 2009

(65) Prior Publication Data
US 2010/0285554 A1    Nov. 11, 2010

(51) Int. Cl.
*C12P 7/10* (2006.01)
*C12P 7/08* (2006.01)
*A61K 36/00* (2006.01)

(52) U.S. Cl. .......................... 435/165; 435/163; 424/725
(58) Field of Classification Search .................. None
See application file for complete search history.

(56) References Cited

U.S. PATENT DOCUMENTS

| | | | |
|---|---|---|---|
| 4,324,068 A | 4/1982 | Anthony | |
| 4,532,210 A | 7/1985 | Miura et al. | |
| 6,395,521 B1 | 5/2002 | Miura | |
| 7,135,308 B1* | 11/2006 | Bush et al. ....................... | 435/42 |
| 2003/0024874 A1 | 2/2003 | Wallace | |
| 2005/0061737 A1 | 3/2005 | Linden et al. | |
| 2008/0176304 A1 | 7/2008 | Lee | |
| 2010/0285551 A1* | 11/2010 | Hagen ........................... | 435/161 |
| 2011/0045561 A1 | 2/2011 | Hagen | |
| 2011/0086400 A1 | 4/2011 | Hagen | |
| 2011/0086401 A1 | 4/2011 | Hagen | |
| 2011/0086419 A1 | 4/2011 | Hagen | |

OTHER PUBLICATIONS

Li, Y., Xie, Y., Ren, B., Luo, W., and Huang, J. (2007) Oxygen enhances the recovery of Potamogeton maackianus frum prolonged exposure to very low irradiance. Aquatic Botany 86: 295-299.*
Mishima, D., Kuniki, M., Sei, K., Soda, S., Ike, M. and Fujita, M. (2007) Ethanol production from candidate energy crops: Water hyacinth (*Eichnornia crassipes*) and water lettuce (*Pistia stratiotes L.*) Bioresource Technology 99: 2495-2500.*
Summers, J.E., Ratcliffe, R.G., and Jackson, M.B. (2000) Anoxia tolerance in aquatic monocot Potamogeton pectinatus: absence of oxygen stimulates elongation in association with an unusually large Pasteur effect. J. Exper. Botany vol. 51, No. 349, pp. 1413-1422.*
Li, Y., Xie, Y., Ren, B., Luo, W., and Huang, J. (2007) Oxygen enhances the recovery of Potamogeton maackianus from prolonged exposure to very low irradiance. Aquatic Botany 86; 295-299.*
Miura, et al. (1993) Applied Biochemistry and Biotechnology vol. 39/40 pp. 753-761.*
Dixon et al. (2006) Plant Cell Physiol. Jan;47(1): 128-40. (Epub Nov. 12, 2005).*
Janssen et al. (2000) J. Applied Phycology 12: 225-237.*
Journal of Experimental Botany vol. 51, No. 349 pp. 1413-1422 Aug. 2000.
Aquatic Botany 86 (2007) 295-299.
Mishima, D. et al., Ethanol production from candidate energy crops: Water hyacinth (*Eichnornia crassipes*) and water lettuce (*Pistia stratiotes L.*) Bioresource Technology 99:2495-2500.
International Search Report issued in PCT/US2010/058174, mailed Aug. 30, 2011.
International Search Report issued in PCT/US2010/033335, mailed Dec. 17, 2010.
Mishima, D. et al., Ethanol production from candidate energy crops: Water hyacinth (*Eichnornia crassipes*) and water lettuce (*Pistia stratiotes* L.) Bioresource Technology 99:2495-2500, (2008).
Ailstock,M. Stephen "The Characterization of Axenic Culture Systems Suitable for Plant Propagation and Experimental Studies of the Submersed Aquatic Angiosperm *Potamogeton pectinatus* (Sago Pondweed)" vol. 14, No. 1, p. 57-64 Mar. 1991.
Anderson, Lars W.J., "A review of aquatic weed biology and management research conducted by the United States Department of Agriculture—Agricultural Research Service" Pest Manag Sci 59:801-813 (online: 2003) DOI: 10.1002/ps.725.
Baldantoni, Daniela, "Analyses of three native aquatic plant species to assess spatial gradients of lake trace element contamination" Aquatic Botany 83 (2005) 48-60.
Colmer, T.D., "Root aeration in rice (*Oryza sativa*): evaluation of oxygen, carbon dioxide, and ethylene as possible regulators of root acclimatizations" New Phytologist (2006) 170: 767-778.
Colmer, Timothy, "Blackwell Publishing Ltd Underwater photosynthesis and respiration in leaves of submerged wetland plants: gas films improve $CO_2$ and O2 exchange" New Phytologist (2008) 177: 918-926.
Crump, Byron, "Attached Bacterial Populations Shared by Four Species of Aquatic Angiosperms" Applied and Environmental Microbiology, Oct. 2008, p. 5948-5957 vol. 74, No. 19.
Dixon, M.H., "Physiological and Metabolic Adaptations of *Potamogeton pectinatus* L. Tubers Support Rapid Elongation of Stem Tissue in the Absence of Oxygen" Plant Cell Physiol. 47(1): 128-140 (2006).
Ghobrial, M.G., "Influence of Barley Straw and Submerged Macrophytes on Fishpond Wastewater Quality" vol. 33 No. 3, 2007: 68-87.
Greger, Maria, et al., "A Tentative Model of Cd Uptake in *Potamogeton Pectinatus* in Relation to Salinity" vol. 35, No. 2, pp. 215 225, 1995.

(Continued)

*Primary Examiner* — Chris R Tate
*Assistant Examiner* — Russell Fiebig
(74) *Attorney, Agent, or Firm* — Faegre Baker Daniels LLP

(57) ABSTRACT

A method of stimulating ethanol production and growth of aquatic plants includes the steps of placing aquatic plants in a cell containing water and creating an anoxic condition within the pool to initiate an anaerobic process by the aquatic plants. The aquatic plants increase in size and release ethanol by metabolism of stored carbohydrates during the anaerobic process. An oxygenated condition is then created within the cell to initiate an aerobic process. The aquatic plants create and store carbohydrates during the aerobic process. The steps of creating anoxic and oxygenated conditions are repeated to stimulate increased aquatic plant size and to increase the release of ethanol.

6 Claims, 1 Drawing Sheet

OTHER PUBLICATIONS

Gruber, Renee., et al.,"Feedback effects in a coastal canopy-forming submersed plant bed" Limnol. Oceanogr., 55(6), 2010, 2285-2298.

Hangelbroek, Helen H. et al., "Local adaptation of the pondweed *Potamogeton pectinatus* to contrasting substrate types mediated by changes in propagule provisioning" Journal of Ecology 2003 91, 1081-1092.

Harada, Taro, et al., "Anoxia-enhanced expression of genes isolated by suppression subtractive hybridization from pondweed (*Potamogeton distinctus* A. Benn.) turions" Planta (2007) 226:1041-1052.

Harada, Taro, et al.. "Expression of Sucrose Synthase Genes Involved in Enhanced Elongation of Pondweed (*Potamogeton distinctus*) Turions under Anoxia" Annals of Botany 96: 683-692, 2005.

Harada, Taro, et al., "Starch Degradation and Sucrose Metabolism During Anaerobic Growth of Pondweed (*Potamogeton distinctus* A. Benn.) Turions" Plant and Soil 253: 125-135, 2003.

Hidding, Bert, et al., "How a Bottom-Dweller Beats the Canopy: Inhibition of an Aquatic Weed (*Potamogeton Pectinatus*) by Macroalgae (*Chara* spp.)", Freshwater Biology (2010) 55, 1758-1768.

Huang, Shaobai, et. al., "Manipulation Of Ethanol Production In Anoxic Rice Coleoptiles By Exogenous Glucose Determines Rates Of Ion Fluxes And Provides Estimates Of Energy Requirements For Cell Maintenance During Anoxia," Journal of Experimental Botany, vol. 56, No. 419, pp. 2453-2463, Sep. 2005.

Ishizawa, K., "Growth and Energy Status of Arrowhead Tubers, Pondweed Turions and Rice Seedlings Under Anoxic Conditions," Plant, Cell and Environment (1999) 22, (505-514).

Jackson, Michael B., "Evolution and Mechanisms of Plant Tolerance to Flooding Stress," Annals of Botany 103: 137-142, 2009.

James, William F., "Effects Of Lime-Induced Inorganic Carbon Reduction On The Growth Of Three Aquatic Macrophyte Species," Aquatic Botany 88 (2008) 99-104.

Kennedy, Thomas L., "The Effects Of Nitrate Loading On The Invasive Macrophyte Hydrilla Verticillata And Two Common, Native Macrophytes In Florida," Aquatic Botany 91 (2009) 253-256.

Koizumi, Yayoi, "Involvement Of Plasma Membrane H+-Atpase in Anoxic Elongation of Stems in Pondweed (*Potamogeton Distinctus*) Turions," New Phytologist © 2011 New Phytologist Trust, doi: 10.1111/j.1469-8137.2010.03605.x, 10 pages.

Miller, Stephanie, A., "Mechanisms Of Resistance Of Freshwater Macrophytes To Herbivory By Invasive Juvenile Common Carp," Freshwater Biology (2007) 52, 39-49.

Ookawara, Ryuto, "Expression of a-Expansin and Xyloglucan Endotransglucosylase/Hydrolase Genes Associated with Shoot Elongation Enhanced by Anoxia, Ethylene and Carbon Dioxide in Arrowhead (*Sagittaria pygmaea* Miq.) Tubers," Annals of Botany 96: 693-702, 2005.

Rozentsvet, O.A., "Lipid Composition of *Potamogeton pectinatus* as a Function of Water Contamination," Chemistry of Natural Compounds, vol. 46, No. 5, 2010.

Sato, Tatsuhisa, "Stimulation of Glycolysis in Anaerobic Elongation of Pondweed (*Potamogeton distinctus*) Turions," Journal of Experimental Botany, vol. 53, No. 376, pp. 1847-1856, Sep. 2002.

Smart, R. Michael, "Techniques for Establishing Native Aquatic Plants," J. Aquat. Plant Manage. 36: 44-49 (1998).

Spencer, David F., "Competition between two submersed aquatic macrophytes, *Potamogeton pectinatus* and *Potamogeton gramineus*, across a light gradient," Aquatic Botany 92 (2010) 239-244.

Spencer, David F., "Construction costs for some aquatic plants," Aquatic Botany 56 (1997) 203-214.

Spencer, David F., "Dilute Acetic Acid Exposure Enhances Electrolyte Leakage by *Hydrilla Verticillata* and *Potamogeton Pectinatus* Tubers," J. Aquat. Plant Manage. 35: 25-30 (1997).

Spencer, David F., "Emergence of vegetative propagules of *Potamogeton nodosus, Potamogeton pectinatus, Vallisneria americana*, and *Hydrilla verticillata* based on accumulated degree-days," Aquatic Botany 67 (2000) 237-249.

Spencer, David F., "Influence Of Propagule Size, Soil Fertility, And Photoperiod On Growth And Propagule Production By Three Species Of Submersed Macrophytes," Wetlands, vol. 15, No. 2, Jun. 1995, pp. 134-140.

Spencer, David F. et al., "Soluble Sugar Concentrations Associated with Tuber and Winter Bud Sprouting", J. Aquat. Plant Manage. 39:45-47 (2001).

Summers, Jacky E., "Anaerobic promotion of stem extension in *Potamogeton pectinatus*. Roles for carbon dioxide, acidification and hormones," Physrologia Plantarum 96: 615-622. 1996.

Summers, Jacky E., "Light- And Dark-Grown *Potamogeton Pectinatus*, An Aquatic Macrophyte, Make No Ethylene (Ethene) But Retain Responsiveness To The Gas," Aust. J. Plant Physiol., 1998, 25, 599-608.

Sutton, David L., "Influence of Allelochemicals and Aqueous Plant Extracts on Growth of Duckweed," J. Aquat. Plant Manage. 27: 90-95 (1989).

Tamura, Shinsuke, "Involvement of Calcium Ion in the Stimulated Shoot Elongation head Tubers under Anaerobic Conditions," Plant Cell Physiol. 42(7): 717-722 (2001).

Tauskela, Joseph S., "A Regulated Environmental Perfusion System For The Study Of Anoxic Or Hypoxic Cultured Neurons Using Microfluorescence Imaging And Electrophysiology," pnugers Arch—Eur J Phys;ol (1998) 435: 775-780.

Van Den Berg, Marcel S., "Competition between *Chara aspera* and *Potamogeton pectinatus* as a function of temperature and light," Aquatic Botany 60 (1998) 241-250.

Voesenek, L.A.C.J., "The Role Of Ethylene And Darkness In Accelerated Shoot Elongation Of *Ammophila Breviligulata* Upon Sand Burial," Oecologia (1998) 115:359-365.

Winkel, Anders., "Use Of Sediment $CO_2$ By Submersed Rooted Plants," Annals of Botany 103: 1015-1023, 2009.

Woolf, Thomas E., "Seasonal Biomass and Carbohydrate Allocation Patterns in Southern Minnesota Curlyleaf Pondweed Populations," J. Aquat. Plant Manage. 41: 113-118 (2003).

Ueno, Yoshiyuki et al., "Ethanol Production by Dark Fermentation in the Marine Green Alga, *Chlorococcum littorale*", Journal of Fermentation and Bioengineering, vol. 86, No. 1, 38-43, 1998.

Written Opinion issued in PCT/US2010/033335, mailed Dec. 17, 2010, 4 pages.

\* cited by examiner

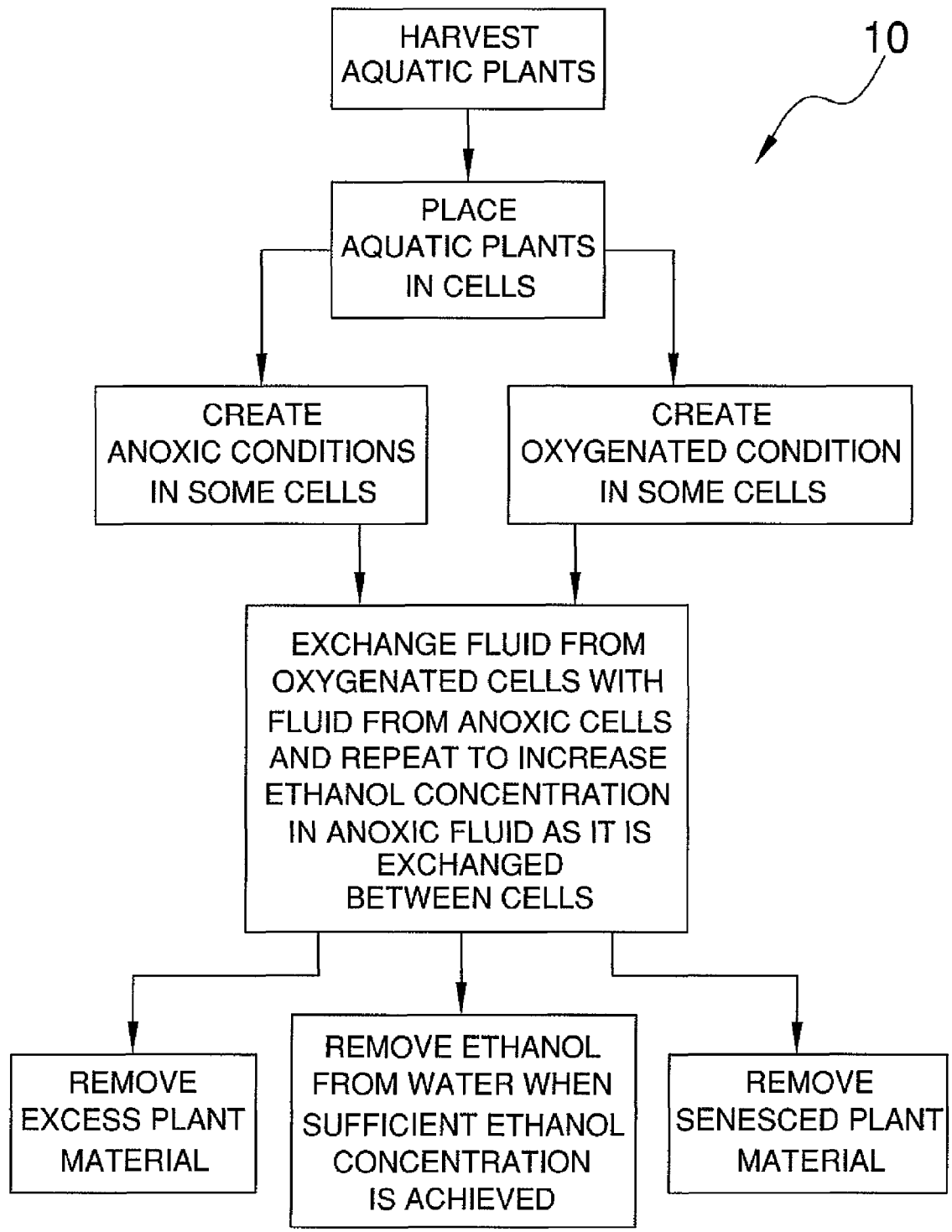

METHOD OF STIMULATING ETHANOL PRODUCTION AND GROWTH OF AQUATIC PLANTS

BACKGROUND OF THE DISCLOSURE

Field of the Disclosure

The disclosure relates to ethanol production methods and more particularly pertains to a new ethanol production method for promoting plant growth by plants which produce free ethanol during anaerobic metabolism to form a self-sustaining cycle of plant growth and ethanol production.

SUMMARY OF THE DISCLOSURE

An embodiment of the disclosure meets the needs presented above by generally comprising the steps of placing aquatic plants in a cell containing water and creating an anoxic condition within the pool to initiate an anaerobic process by the aquatic plants. The aquatic plants increase in size and release ethanol by metabolism of stored carbohydrates during the anaerobic process. An oxygenated condition is then created within the cell to initiate an aerobic process. The aquatic plants create and store carbohydrates during the aerobic process. The steps of creating anoxic and oxygenated conditions are repeated to stimulate increased aquatic plant size and to increase the release of ethanol.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawing wherein:

FIG. 1 is a schematic view of a method of stimulating ethanol production and growth of aquatic plants according to an embodiment of the disclosure.

DESCRIPTION OF THE PREFERRED EMBODIMENT

With reference now to the drawing, and in particular to FIG. 1, a new ethanol production method embodying the principles and concepts of an embodiment of the disclosure and generally designated by the reference numeral 10 will be described.

As illustrated in FIG. 1, the method 10 of stimulating ethanol production and growth of aquatic plants generally comprises harvesting aquatic plants from lakes or ponds which are then introduced into cells. As the method 10 is performed, it may be used to grow and provide aquatic plants as they are needed for future cells or for replacement purposes. The cells are constructed to hold water and may or may not be lined to prevent transfer of fluids and gases into a ground surface supporting the cell. A fine particulate is placed in the cells and the aquatic plants introduced into the cells where they can anchor themselves in the particulate. A fine particulate is used as it may promote less energy expenditure on the part of the aquatic plants to root growth into the particulate and retains a higher percentage of the plant matter above the surface of the particulate.

The number of cells and their size is not crucial to the method and each number and size may be dictated by available land area, access to raw materials and cost controls, though it should be understood that the method may be practiced with a single cell. The cells may have any depth required for the chosen aquatic plant to properly grow. However, it has been found that cell may have a depth of between 10 cm and 7 m to prevent restricted plant growth. The cells may also be temperature controlled and in particular the cell should be prevented from freezing which may kill the aquatic plants. Heat for the cells may be sequestered from waste heat emitted by adjacent ethanol processing plants or any other convenient source of waste heat.

The aquatic plants may be selected from any number of aquatic plants which readily live in or on an aquatic environment such as directly in water or in permanently saturated soil. Further, more than one type of aquatic plant may be used within a single cell. The aquatic plants may include, for example, algae, submersed aquatic herbs such as, but not limited to, *Potamogeton pectinatus, Potamogeton crispus, Ruppia maitima, Myriophyllum spicatum, Hydrilla verticillata, Elodea densa, Hippuris vulgaris, Aponogeton boivinianus, Aponogeton rigidifolius, Aponogeton longiplumulosus, Didiplis diandra, Vesicularia dubyana, Hygrophilia augustifolia, Micranthemum umbrosum, Eichhornia azurea, Saururus cernuus, Cryptocoryne lingua, Hydrotriche hottoniiflora, Eustralis stellata, Vallisneria rubra, Hygrophila salicifolia, Cyperus helferi, Cryptocoryne petchii, Vallisneria americana, Vallisneria torta, Hydrotriche hottoniiflora, Crassula helmsii, Limnophila sessiliflora, Potamogeton perfoliatus, Rotala wallichii, Cryptocoryne becketii, Blyxa aubertii* and *Hygrophila difformmis*, duckweeds such as, but not limited to, *Spirodela polyrrhiza, Wolffia globosa, Lemna trisulca, Lemna gibba, Lemna minor*, and *Landoltia punctata*, water cabbage, such as but not limited to *Pistia stratiotes*, buttercups such as but not limited to *Ranunculus*, water caltrop such as but not limited to *Trapa natans* and *Trapa bicornis*, water lily such as *Nymphaea lotus*, Nymphaeaceae and Nelumbonaceae, water hyacinth such as but not limited to *Eichhornia crassipes, Bolbitis heudelotii*, and *Cabomba*, and seagrasses such as but not limited to *Heteranthera zosterifolia*, Posidoniaceae, Zosteraceae, Hydrocharitaceae, and Cymodoceaceae. Moreover, in one of the various embodiments, a host alga is selected from the group consisting of green algae, red algae, brown algae, diatoms, marine algae, freshwater algae, unicellular algae, multicellular algae, seaweeds, cold-tolerant algal strains, heat-tolerant algal strains, ethanol-tolerant algal strains, and combinations thereof.

The aquatic plants in general may also be selected from one of the plant families which include Potamogetonaceae, Ceratophyllaceae, Haloragaceae, and Ruppiaceae. More particularly, the aquatic plants chosen should have a large Pasteur effect which increases the ratio of anaerobic $CO_2$ production to the aerobic $CO_2$ production. Typically this ratio is on the order of 1:3, but aquatic plants such as for example *Potamogeton pectinatus*, commonly known as Sago Pondweed, may increase this ratio to 2:1 as explained in "Anoxia tolerance in the aquatic monocot *Potamogeton pectinatus*: absence of oxygen stimulates elongation in association with an usually large Pasteur effect," Journal of Experimental Botany, Volume 51, Number 349, pp. 1413-1422, August 2000, which is incorporated herein by reference. During an elongation process which takes place in an anoxic environment, the plant elongates to form cellular chambers which will later be used to store carbohydrates formed during aerobic metabolism through an aerobic process of the aquatic plant. These carbohydrates can then be used to release ethanol during anaerobic metabolism through an anaerobic process of the aquatic plant. Generally, the equations are as follows:

Aerobic plant metabolism: $6CO_2 + 6H_2O \rightarrow 6O_2 + C_6H_{12}O_6$

Anaerobic plant metabolism: $C_6H_{12}O_6 \rightarrow 2CO_2 + 2C_2H_5OH$

Once the aquatic plants are in a cell, the water in the cell is placed in an anoxic condition by introducing, originally or at a later time, anoxic water into the cell. Alternatively, corn and/or bacteria may be added to the water to deplete the oxygen in the water. The lack of oxygen in the water initiates the anaerobic process in the aquatic plants causing them to elongate and to produce ethanol. This may be encouraged by the introduction of chemical catalysts and $CO_2$. One chemical catalyst which may be included is 2,4-dichlorophenoxyacetic acid. Additional nutrients and salts such as salts of potassium, nitrogen and phosphorus may further be added to promote growth of the aquatic plants. Further, depending upon the species of aquatic plant being utilized, organic substrates, including but not limited to those such as sucrose, glucose and acetate, may also be added to the cell.

During the anaerobic process, the aquatic plants will increase in size dramatically and may achieve a lengthening of up to 10 times or more of its original length. The term 'size' here is to be understood to include a volume increase of plant matter which allows for it to store a larger amount of carbohydrates. This elongation provides cellular chambers for holding carbohydrates to be later formed by the aquatic plants. Additionally during the anaerobic process, ethanol is excreted extracellularly by the aquatic plants. This ethanol is then held within the water of the cell until it is removed by conventional methods. As explained further below, the cell, when first used, may be allowed to achieve a minimum ethanol concentration which will be determined depending on the particular method being practiced. This minimum concentration will be increased through progression of the method. This step may take place from one to several days though in the case of *Potamogeton pectinatus* a total of six days may suffice. The time required will depend on many factors such as light diffusion and availability of nutrients.

The next step is to stop the anaerobic process by creating an oxygenated condition within the cell which will initiate the aerobic process. This may be accomplished by introducing oxygenated water into the cell and by removing the anoxic water. During the aerobic process, as indicated above, the aquatic plants create carbohydrates through metabolic processes and then retain the carbohydrates within their elongated structures. Waste materials, such as waste biomass from the method 10, industrial waste, municipal waste and the like may be added to the cell to provide nutrients to the aquatic plants. Additionally, maximum sunlight filtration is encouraged as is temperature regulation to promote growth of the aquatic plants. Further, the pH of the cell must be monitored to prevent $CO_2$ acidosis of the cell. This may be counteracted with calcium buffering compounds such as calcium carbonate and calcium chlorate, but will ultimately be dependent upon the tolerances of the particular aquatic plant species in the cell. The duration of the aerobic process is likewise dependent upon a number of factors but will typically end when carbohydrate production begins to slow. With *Potamogeton pecti-*

*natus*, this may be between 2 days and 14 days depending upon environmental conditions within the cell.

The use of anoxic and oxygenated water may also be combined by use of thermal strata within the cell. In particular, the coldest strata, which will be on the bottom of the cell, may remain anoxic to encourage growth while the upper strata of warmer water may include oxygenated water to encourage the aerobic process.

Once maximum carbohydrate formation is approached the oxygenated water is removed and is replaced again with anoxic water to again begin the process of elongation and ethanol formation. The steps of adding anoxic water and oxygenated water are then repeated to continually promote elongation and ethanol production followed by carbohydrate production. This creates a self-sustaining cycle as the plant growth replenishes both plant matter lost to plant senescence and those plants which no longer meet established tolerances of ethanol production. Additional plant growth which cannot be used for replenishing purposes or for furnishing plant material for another cell may be removed and fermented using conventional methods to also produce ethanol. Carbon dioxide released during the fermentation process may be captured and returned to the cell to promote carbohydrate production. Plant waste, both before or after the fermentation process, may further be used for replenishing nutrients to the cell and/or may be processed for biochemical industrial usage such as in ethanol and diesel biofuels, pharmaceuticals, cosmetics, colorants, paints and the like.

As stated above, the anoxic water may be retained and used again, at least until its ethanol content approaches a lethal concentration to the aquatic plant. This concentration is dependent upon the aquatic plant being used as well the number of cells being utilized which can affect the number of times the anaerobic process can occur. Typically the method will be practiced with multiple cells wherein the anoxic water and the oxygenated water are rotated between the cells as needed to alternate between the anoxic condition and the oxygenated condition. For example, the process of utilizing multiple cells may include a first cell having anoxic water containing 2% ethanol which is moved into a second cell having previously been oxygenated. The anoxic water replaces the removed oxygenated water in the second cell to create an anoxic condition in the second cell. Within the second cell plant growth and ethanol production are then stimulated. It is noted that having ethanol originally in the second cell (since the anoxic water contains ethanol from the anaerobic process of the first cell) may further spur ethanol production when the aquatic plants detect ethanol in the water. The ethanol concentration may be allowed to increase, for example, up to 4% in the second cell. Each time the anoxic water is moved into a new cell, the elongation and ethanol production of those plants is stimulated. Once the ethanol concentration of the anoxic water reaches a predetermined level, such as for example 10% by volume, the anoxic water is removed from the cell it is now positioned in and the ethanol extracted from the water using conventional means.

The use of multiple cells allows the cycle to be used within a closed loop which again is self sustaining and will sequester carbon dioxide during the formation of carbohydrates. The method 10 grows new aquatic plants faster than they are depleted by senescing to allow for new cells to be seeded by the newly grown aquatic plants. More importantly, all plant waste may be utilized through fermentation into ethanol and processed for biochemical industries or returned to the cells as feed material.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

I claim:

1. A method of recovering ethanol from an aquatic plant, said method comprising the steps of:
 placing at least on aquatic plant selected from the family Potamogetonaceae in a container containing water,
 creating and maintaining an anoxic condition within said water to initiate and maintain anaerobic plant metabolism while inhibiting aerobic plant metabolism therein to produce ethanol, said aquatic plants releasing ethanol into the water during said anoxic condition,
 creating and maintaining and oxygenated condition within said water to initiate and maintain aerobic plant metabolism to produce and store carbohydrates while inhibiting anaerobic plant metabolism during said oxygenated condition,
 repeating the steps of creating and maintaining anoxic and oxygenated conditions one or more times to repeatedly release ethanol into the water,
 recovering ethanol from said water.

2. The method according to claim 1, further including the step of introducing catalysts to said container prior to the step of creating and maintaining an anoxic condition.

3. The method of claim 1, wherein the step of introducing catalysts includes the step of adding 2,4-dichlorophenoxyacetic acid.

4. The method of claim 1, further including the step of adding $CO_2$ to said container prior to the step of creating and maintaining an oxygenated condition.

5. The method of claim 1, further including the steps of:
 placing the at least on aquatic plant in at least one additional container; and
 transferring said anoxic water between the containers to increase a concentration of ethanol in said anoxic water.

6. The method of claim 1, further including the step of introducing plant nutrients into said container to increase creation of carbohydrates during the step of creating and maintaining an oxygenated condition.

* * * * *